United States Patent [19]

Dove et al.

[11] Patent Number: 5,157,113
[45] Date of Patent: Oct. 20, 1992

[54] REMOVAL OF NUCLEIC ACIDS FROM MONOCLONAL ANTIBODY PREPARATIONS

[75] Inventors: George Dove, Hercules; Gautam Mitra, Kensington, both of Calif.

[73] Assignee: Miles Inc., Elkhart, Ind.

[21] Appl. No.: 684,415

[22] Filed: Apr. 12, 1991

Related U.S. Application Data

[63] Continuation of Ser. No. 83,136, Aug. 10, 1987.

[51] Int. Cl.$^5$ .................... C07K 3/12; C07K 3/28; C07K 15/28
[52] U.S. Cl. .................................... 530/412; 514/2; 514/12; 514/21; 530/387.1; 530/388.1; 530/416; 530/417; 530/418; 530/419; 530/420; 530/421; 530/863; 530/864; 424/85.8
[58] Field of Search .................... 514/2, 12, 21; 424/85.8; 530/412, 414, 416, 417, 418, 421, 427, 387, 387.1, 388.1, 419, 420; 935/19

[56] References Cited

U.S. PATENT DOCUMENTS

| | | | |
|---|---|---|---|
| 4,172,124 | 10/1979 | Koprowski et al. | 424/85 |
| 4,271,145 | 6/1981 | Wands et al. | 424/85 |
| 4,272,521 | 6/1981 | Zuffi | 424/85 |
| 4,318,902 | 3/1982 | Stephan | 424/85 |
| 4,464,465 | 8/1984 | Lostrom | 435/68 |
| 4,604,235 | 8/1986 | Flashner | 530/387 |

FOREIGN PATENT DOCUMENTS

| | | |
|---|---|---|
| 0038667 | 10/1981 | European Pat. Off. . |
| 5320493 | 2/1978 | Japan . |
| 5549834 | 12/1980 | Japan . |
| 82/01072 | 4/1982 | PCT Int'l Appl. . |

OTHER PUBLICATIONS

WPI Abstract of JP 53-20494 Feb. 24 (1978).
WPI Abstract, Mitsubishi Gas Chem Ind., JP 53-020493 Feb. 24, 1978.
Dove et al., Abstr. Pap. Am. Chem. Soc. 198th Meeting MBTD 26, 1989.
Newkirk et al., Hybridoma, vol. 6, No. 5 pp. 453-460 (1987).
Scopes, Protein Purification—Principles and Practice, Second Edition (Springer-Verlag New York, Inc.) pp. 62-63 (1987).
Clezardin et al.; J. Chromatog., vol. 319 pp. 67-77 (1985).
Sugg et al., "On the Problems of Efficacy of Separation of IgM and IgG by Different Methods", 36 Vox Sang. 25-28 (1979).
Wichman et al., "Purification of Human Immunoglobulin M by Affinity Chromatography on Protamine-Sepharose", 490 Biochem. Biophys. Acta 363-369 (1977).
Sampson et al., "The Separation of Immunoglobulin M from Human Serum by Fast Protein Liquid Chromatography", 69 J. Immuno. Meth., 9-15 (1984).

(List continued on next page.)

Primary Examiner—Merrell C. Cashion, Jr.
Assistant Examiner—Andrew G. Kozycki
Attorney, Agent, or Firm—Elizabeth F. Enayati; James A. Giblin

[57] ABSTRACT

An essentially pure and stablized antibody preparation comprising IgM antibodies having a purity greater than about 98% by weight and a nucleic acid content of less than about 200 pg per mg IgM. In one embodiment IgM antibodies from a monoclonal source are subjected to ion exchange and size exclusion chromatography at an alkaline pH to yield a purified IgM having a nucleic acid content of less than 10 pg/mg IgM, preferably less than about 4 pg/mg IgM. A highly purified and stabilized preparation of anti Pseudomonas aeruginosa antibodies is disclosed. The removal of nucleic acids is assured by subjecting the antibody source to at least one and preferably two low pH precipitation steps. In a very preferred embodiment, ion exchange and/or size exclusion chromatography is used to remove any residual nucleic acids.

11 Claims, 1 Drawing Sheet

OTHER PUBLICATIONS

Köhler and Milstein, "Continuous Cultures of Fused Cells Secreti Antibody of Predefined Specificity", 256 Nature 495–497 (1975).

Steinbuch et al., "Preparation of an IgM and IgA Enriched Fraction for Clinical Use", 3(4) Preparative Biochemistry 363–373 (1973).

Burchiel et al., "Rapid and Efficient Purification of Mouse Monoclonal Antibodies from Ascites Fluid Using High Performance Liquid Chromatography", 69 J. Immuno. Meth., p. 33 (1984).

Deschamps et al., "A High-Performance Liquid Chromatographic Procedure for the Purification of Mouse Monoclonal Antibodies", 147 Anal. Biochem. p. 451 (1985).

Brooks et al., "Preparative HPLC Purification of IgG and IgM Monoclonal Antibodies", Amer. Lab. (Oct. 1985).

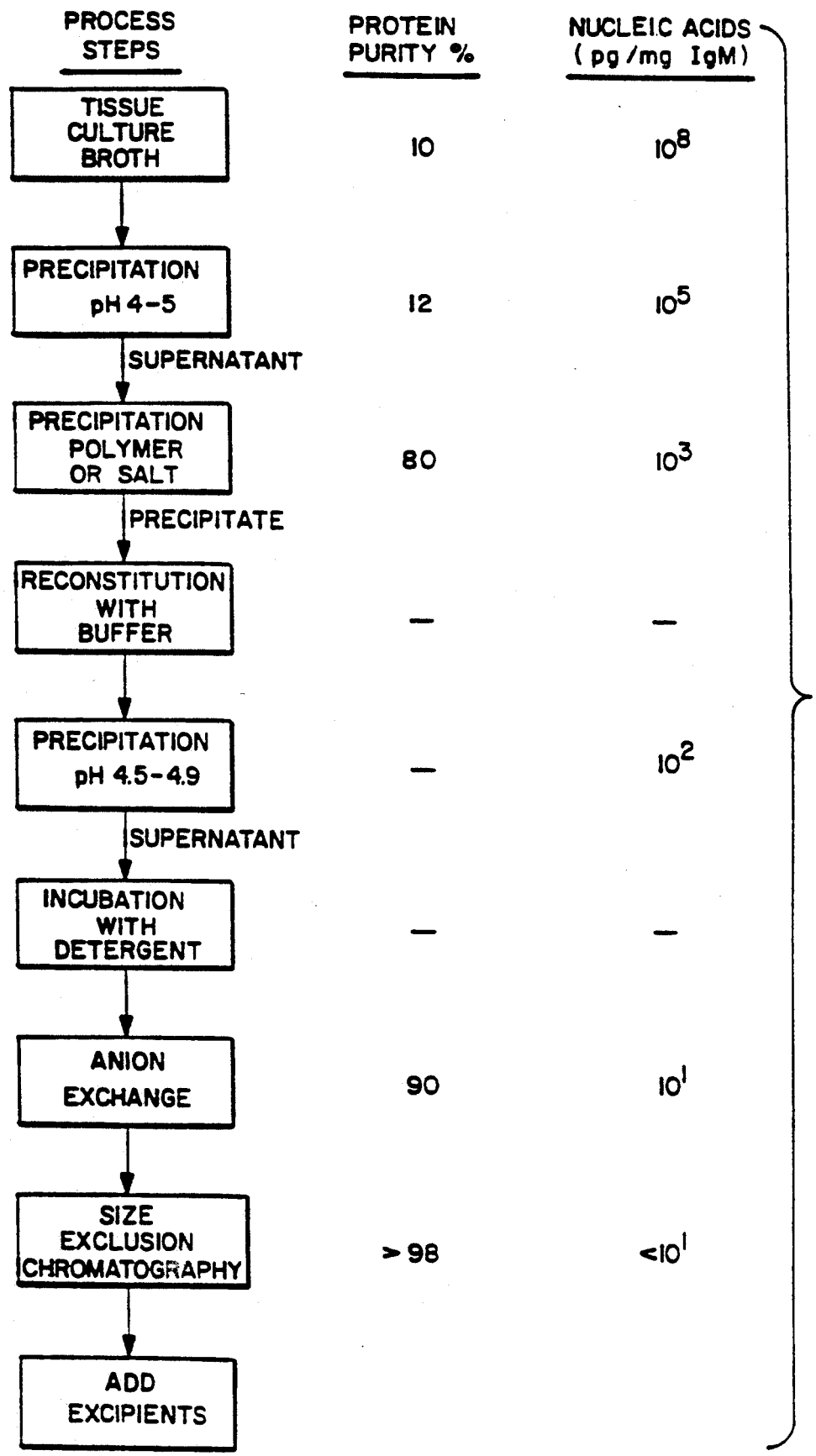

REMOVAL OF NUCLEIC ACIDS FROM MONOCLONAL ANTIBODY PREPARATIONS

REFERENCE TO RELATED APPLICATIONS

This is a continuation application of U.S. Ser. No. 07/083,136, entitled "Purified IgM", filed on 10 Aug. 1987.

BACKGROUND OF THE INVENTION

1. Field

This disclosure is concerned generally with purified immunoglobulins and specifically with a highly purified immunoglobulin of the IgM class which is substantially free of nucleic acids.

2. Prior Art

IgM is a well known 19S immunoglobulin which comprises about 7% of the immunoglobulins found in man. IgM antibodies are said to have an antibody valence of at least five and they are the earliest antibodies generated in an immune response. Although IgM antibodies tend to be very effective, especially in combating bacterial infections, they have a relatively short in vivo half life of about five days. Further, IgM antibodies are labile and relatively difficult to stabilize, especially in purified form.

Various purification schemes have been suggested for plasma-derived IgM and, more recently, monoclonal-derived IgM. In the case of plasma-derived IgM, it has been known since the 1940's that alcohol fractionation techniques could be used to obtain a relatively concentrated IgM from what is known as Rohn Fraction . See for example U.S. Pat. No. 4,318,902 (and the cited references) to W. Stephan and concerned with the use of beta-propriolactone to make a concentrated IgM suitable for intravenous (IV) administration. In addition, see EPO application 0 038 667 of Miura et al (IgM acylation). See also, U.S. Pat. No. 4,272,521 to Zuffi concerned with the purification of immune serum globulins in general by using ion exchange resins at an alkaline pH. Other IgM purification or preparation techniques are disclosed by U. Sugg et al, Vox Sang. 36:25-28 (1979); M. Steinbach et al, Preparative Biochemistry 3(4), 363–373 (1973) and A. Wichman et al, Biochem. Biophys. Acta 490:363 –69 (1977). Techniques for making specific monoclonal antibodies of the IgM type are shown in U.S. Pat. No. 4,271,145 to Wands et al. A specific immunoassay using high affinity IgM antibodies is disclosed in W 082/01072 published in the names of Wands et al. See also, I. A. Sampson et al, J. Immuno. Meth. 69, pp. 9-15, 1984. For a variety of technical reasons, plasma derived IgM has been relatively difficult to purify and the highest known purity to dare is about 90% IgM, by weight. Also, the nucleic acid content of such plasma derived IgM has generally not been a serious concern because the IgM is derived from a human plasma source.

Typical nucleic acid contents for plasma-derived IgM are thought to be in the range of about 1 ng to 10 μg per mg.

Since the publication by Köhler and Milstein, "Continuous Cultures of Fused Cells Secreting Antibody of Predefined Specificity", Nature 256:495–497 (1975), the production of monoclonal antibodies has become well known. Monoclonal antibodies of a given specificity are now routinely made using somatic cell hybrids (see, for example, U.S. Pat. No. 4,172,124 to H. Koprowski et al), using EBV transformed cells (see, for example, U.S. Pat. No. 4,446,465 to M. Lostrom), a combination of the two or by the electrofusion of cells. Monoclonals of both the IgG and IgM classes have been made, purified and characterized. Such IgM preparations are described by D. Nau, Biochromatography, 1, No. 2, pp. 83-84 (95% pure IgM from tissue culture); M. Fishner, U.S. Pat. No. 4,604,235 (90% pure IgM from mouse asciter fluid and which was characterized as "essentially pure antibody"); J. R. Wands et al, W 082/01072 (high affinity IgM monoclonal antibodies for diagnostics, cited above); S. Burchiel, et al, J. Immuno. Meth., 69, p. 33, 1984 (IgG purified from mouse asciter fluid); J. Deschamps et al, Anal. Biochem. 147, p. 451, 1985 (IgG from mouse asciter fluid); and T. Brooks et al, Amer. Lab., October, 1985 (use of hydroxyapatite for purification of mouse and human IgG and IgM). Although efforts have been made to purify IgM obtained from monoclonal sources, the highest reported IgM purity to date is about 95% (see Nau, above).

The preparation of a monoclonal IgM against *P. aeruginosa* has been disclosed and IgM derived from a human lymphoblastoid tissue culture and DEAE Sephacel has been used for an initial purification of the IgM. Therapeutically acceptable isotonic solutions of IgM with a concentration of 0.005 to 0.5 ug/ml are known but no data has been given on the relative purity of the IgM product or its formulation.

Although nucleic acid content of plasma-derived IgM has not aroused significant concern, the nucleic acid content of monoclonal IgM is very significant because of the potential danger of introducing foreign (non-human) nucleic acid into a human via a parenterally administered product. Hence, in addition to the desirability of obtaining a purified and concentrated IgM product, it is also desirable to obtain such a product with no or very little nucleic acid. We have now found that such a purified product can be prepared and stabilized by carefully controlling the processing steps and storage conditions. Details of our highly purified IgM are described below.

SUMMARY OF THE INVENTION

Our disclosure is concerned with an essentially pure and stabilized IgM antibody product comprising IgM antibodies having a purity greater than about 98% by weight and a nucleic acid content of less than about 200 pg per mg IgM. In preferred embodiments, the IgM purity is greater than 98% by weight, the nucleic acid content is less than 10 pg per mg IgM, preferably as low or lower than about 4 pg per mg IgM, and the preparation is stabilized by maintaining at a pH ranging from about 4 to 10, preferably at a pH of about 8 in the presence of NaCl and albumin as stabilizers. An illustrative preparation having the above characteristics comprises one or more IgM antibodies specific to serotypic determinants found on the surface of *Pseudomonas aeruginosa* bacteria. The preparation comprises IgM antibodies obtained from one or more clones and it is contemplated that it will be found useful in treating infections of *P. aeruginosa*. The preparation may be obtained by culturing a monoclonal antibody source, harvesting the monoclonal antibodies and then subjecting the harvested antibodies to a carefully controlled series of processing steps which include ion exchange and size exclusion chromatography.

The high purity and low nucleic acid content of the antibodies are obtained by subjecting a source for the antibodies (e.g., a tissue culture broth which includes expressed monoclonal antibodies) to at least one low pH precipitation step at a pH of about 4–5. Preferably, at least two such low pH precipitation steps are used, the first at a pH of 4 to 5 and the second at a pH of 4.5 to 4.9. Further, any residual nucleic acid content (e.g., about $10^1$ pg/mg of antibody) can be removed using ion exchange and/or size exclusion chromatography.

As used herein, the expression nucleic acids refers to DNA or RNA obtained from a foreign source (i.e., animal origin or human cells that have been genetically altered as, for example, by EBV transformation).

BRIEF DESCRIPTION OF THE FIGURE

The FIG. is a flow chart showing the general process steps used to prepare one embodiment of this disclosure. Also shown are the successive increases in purity and decreases in nucleic acid content resulting from individual steps of the overall process.

SPECIFIC EMBODIMENTS

A very important aspect of this disclosure is overall purity, stability and low nucleic acid content of our IgM preparation. As used herein, the expression "essentially pure and stabilized IgM" refers to an IgM preparation comprising IgM antibodies having a purity greater than about 98% by weight and a nucleic acid content of less than about 200 pg per mg of IgM. A "stabilized IgM preparation" means a preparation for which there is less than a 10% change (+ or −) in molecular weight distribution as measured by size exclusion chromatography over a period of at least 6 months (e.g., Pharmacia FPLC—Superose TM 6 peak area). The IgM antibodies are biologically active (capable of forming immunocomplexes) and stabilized by maintaining them at a pH ranging from about 4 to 10 in the presence of suitable stabilizing agents such as NaCl, albumin or amino acids. Although the reduced nucleic acid content is desirable in obtaining near homogeneity of the IgM preparation, regardless of IgM source, it is especially desirable in any IgM product obtained from cultures (e.g. of hybridoma or transformed cells) because of the importance of assuring the absence or near absence of nucleic acids (DNA or RNA) from a foreign source (animal origin or even human cells that have been genetically altered as, for example, by EBV transformation).

The illustrative examples below show an essentially pure and stabilized IgM specific to certain serotypes of *Pseudomonas aeruginosa* bacteria. The IgM antibodies which we were able to purify and stabilize were generated from the following A.T.C.C. clones: line 6F11, Fisher Type 2, A.T.C.C. Accession No. CRL 8562, line 5G2, Fisher Type 6, A.T.C.C. Accession No. CRL 8797, and line 13Cl, Fisher Type 5, A.T.C.C. Accession No. CRL 8796.

MATERIALS AND METHODS

The following examples illustrate that monoclonal antibodies of class M and various Fisher types may be purified to high degree from tissue culture broths.

Example 1

Cell line 6F11, A.T.C.C. Accession.No. CRL 8562 is a human lymphoblastoid cell producing monoclonal antibodies of class M specific to Fisher type 2 *Pseudomonas aeruginosa*. The line was grown in a mixture of Hana Biologics complex media supplemented with human serum albumin, insulin, and transferring. The fermenter was a stirred tank.

A volume of 40 liters at 50 mg/l IgM obtained from the above culture was filtered through a 0.2 um filter (Microgon). The filtrate was concentrated on a tangential flow membrane of 100,000 molecular weight cut-off (Millipore) to 1 liter. The concentrate was cooled to 5° C. and adjusted to pH 7.4. 100 g PEG was added and stirred for 1 hour. The solution was centrifuged at 10,000 × g for 30 minutes. The supernatant was discarded and the precipitate was frozen at −35° C.

The precipitate was resuspended in 1 liter of buffer (0.05 M TRIS, 0.08 M NaCl, pH 8.0). The pH was lowered to 4.5. The solution was centrifuged at 10,000 ×g for 30 minutes and the precipitate was discarded. The supernatant was readjusted to pH 8.0. The solution was bound to an anion exchange column of 1 liter DEAE-Sepharose Fast-Flow (Pharmacia) equilibrated with buffer (0.05 M TRIS, 0.08 M NaCl,.2% Tween, pH 8.0). The IgM was eluted by linear gradient with buffer (0.05 M TRIS, 1.0 M NaCl, pH 8.0). The eluate was concentrated on 100,000 m.w. membrane to 0.5 liters. The concentrate was fractionated on a size exclusion column of Sepharose CL-6B (Pharmacia) equilibrated with buffer (0.5 M NaCl, 0.05 M Tris, 0.01 M glycine, pH 8.0. The IgM eluate was 6 liters.

0.5 g human serum albumin was added and the pool was concentrated on 10,000 mw.w. membrane to 0.1 liters. The solution was diafiltered with 0.5 liters of buffer (0.15 M NaCl, 0.05 M TRIS, 0.01 M glycine, pH 8.0). The solution was sterile filtered. A sublot was frozen and lyophilized by a 80 hour cycle (10 hours at −40° C., 20 hours at −20°, 20 hours at −0°, 10 hours at 20°, and 20 hours at 37° C.).

Cumulative yield is 30–35%. The liquid remains clear without precipitation for more than a year at 5° C. The lyophilized product is white and reconstitutes within 3 minutes with water. Purity is greater than 98% by SDS-PAGE and Pharmacia FPLC-Sepharose 6. Nucleic acid content by hybridization probe assay is less than 67 picogram/mg IgM.

EXAMPLE 2

Cell line 5G2, A.T.C.C. Accession No. CRL 8797, is a human lymphoblastoid ce.11 producing monoclonal antibodies of class M specific to Fisher type 6 of *Pseudomonas aeruginosa*. The line was grown by techniques essentially identical to the line in Example 1.

The broth was purified to final product by techniques similar to the line in Example 1, except that the initial 0.2 um filtrate was adjusted to pH 4.0 and held for 2 hours. The solution was readjusted to neutral pH and further steps were resumed (e.g., concentration, etc.). However, the volume of broth was 10 liters at 80 mg/l and other volumes were scaled proportionately. Final formulation buffer was 0.15 M NaCl, 0.01 M glycine, pH 8.0.

Cumulative yield is 30–35%. The liquid remains clear without precipitation for more than 6 months at 5° C. The lyophilized product is white and reconstitutes within 3 minutes with water. Purity is greater than 98% by SDS-PAGE and Pharmacia FPLC-Sepharose 6.Nucleic acid content by hybridization probe assay is less than 8.5 picogram/mg IgM.

EXAMPLE 3

Cell line 13Cl, A.T.C.C. No. 8796, is a human lymphoblastoid cell producing monoclonal antibodies of class M specific to Fisher type 5 *Pseudomonas aeruginosa*. The line was grown by techniques essentially identical to the line in Example 1.

The broth was purified to final product by techniques essentially identical to the line in Example 2. However, the volume of broth was 10 liters at 100 mg/1 and other volumes were scaled proportionately. Final formulation buffer was 0.15 M NaCl, 0.01 M glycine, pH 8.0

Cumulative yield is 30–35%. The liquid remains clear without precipitation for more than 6 months at 5° C. The lyophilized product is white and reconstitutes within 3 minutes with water. Purity is greater than 98% by SDS-PAGE and Pharmacia FPLC-Sepharose 6. Nucleic acid content by hybridization probe assay is less than 4 picogram/mg IgM.

Our general process is outlined in the FIG.

FINAL PRODUCT

It was found that the highly purified product could be stabilized by adjusting it to a concentration ranging from 0.01 mg ml to 50 mg ml and a pH ranging from 4 to 10, preferably in the presence of NaCl, albumin, amino acids or carbohydrates. Final product may be liquid (as above) or lyophilized and subjected to known techniques for inactivation of infectious agents.

Given the above disclosure it is thought that variations will occur to those skilled in the art. Accordingly, it is intended that the scope of the inventions disclosed should be limited only by the following claims.

We claim:

1. A method of removing nucleic acid from an IgM monoclonal antibody preparation comprising the first step of subjecting an aqueous solution of the antibodies to a pH of about 4 to 5 to precipitate nucleic acids from the solution while maintaining an essentially stabilized IgM preparation.

2. The method of claim 1 wherein the first precipitation step is followed by a secondary precipitation step of subjecting the aqueous solution to a pH of about 4.5 to 4.9.

3. The method of claim 2 wherein three is between the first and the secondary pH precipitation steps an intermediate polymer or salt precipitation step to further precipitate the nucleic acids remaining in the aqueous solution following the first precipitation step.

4. The method of claim 1 wherein after the first precipitation step, the solution of antibodies is subjected to ion exchange to remove residual nucleic acids.

5. The method of claim 1 wherein after the first precipitation step, the solution of antibodies is subjected to size exclusion chromatography to remove residual nucleic acids.

6. The method of claim 1 wherein after the first precipitation step, the solution of antibodies is subjected to ion exchange and size exclusion chromatography to remove residual nucleic acids.

7. A method of purifying a solution of a tissue culture broth containing both antibodies of the IgM type and nucleic acids to obtain an IgM antibody purity of at least 98% and a nucleic acid content of less than 200 pg/mg of IgM antibody, the method comprising the steps of:

(a) subjecting the tissue culture broth to a pH of about 4 to 5 to obtain a first precipitate and a supernatant solution;

(b) subjecting the supernatant solution of step (a) to polymer or salt precipitation to obtain a second supernatant and a second precipitate;

(c) reconstituting the precipitate of step (b) with a buffer solution;

(d) subjecting the reconstituted solution of step (c) to a pH of abut 4.5 to 4.9 to obtain a third precipitate and a third supernatant solution;

(e) incubating the supernatant solution of step (d) with a detergent;

(f) adjusting the pH of the product of step (e) for binding the product to an ion exchange resin;

(g) contacting the solution of step (f) with the ion exchange resin; and (h) subjecting the solution of step (g) to size exclusion chromatography under conditions sufficient to remove remaining nucleic acids.

8. The method of claim 7 wherein the nucleic acid content is less than $10^1$ pg/mg of the IgM antibody.

9. The method of claim 7 wherein the precipitation of step (b) is effected using polyethylene glycol.

10. The method of claim 7 wherein the buffer of step (c) has a pH of about 8.0.

11. The method of claim 7 wherein the size exclusion chromatography is conducted at a pH of about 8.0.

* * * * *